United States Patent
Huckabee et al.

(10) Patent No.: US 7,273,106 B2
(45) Date of Patent: Sep. 25, 2007

(54) SURFACE FLOW CONTROLLED VALVE AND SCREEN

(75) Inventors: Paul Thomas Huckabee, Centennial, CO (US); Phillip Scott Fair, Houston, TX (US); Timothy Peter McPike, Missouri City, TX (US); Edward Eugene Shumilak, II, Houston, TX (US); George Kwok Kai Wong, Houston, TX (US); David Randolph Smith, Kilgore, TX (US)

(73) Assignee: Shell Oil Company, Houston, TX (US)

( * ) Notice: Subject to any disclaimer, the term of this patent is extended or adjusted under 35 U.S.C. 154(b) by 229 days.

(21) Appl. No.: 10/811,211

(22) Filed: Mar. 26, 2004

(65) Prior Publication Data

US 2004/0262011 A1    Dec. 30, 2004

Related U.S. Application Data

(60) Provisional application No. 60/458,617, filed on Mar. 28, 2003.

(51) Int. Cl.
*E21B 43/08*    (2006.01)
*E21B 43/12*    (2006.01)

(52) U.S. Cl. .............. 166/369; 166/66.7; 166/227

(58) Field of Classification Search .......... 166/66.7, 166/227, 236, 369, 386, 332.1
See application file for complete search history.

(56) References Cited

U.S. PATENT DOCUMENTS

| | | | |
|---|---|---|---|
| 5,447,201 A | 9/1995 | Mohn | 166/375 |
| 5,865,251 A * | 2/1999 | Rebardi et al. | 166/278 |
| 5,896,928 A * | 4/1999 | Coon | 166/373 |
| 6,112,817 A * | 9/2000 | Voll et al. | 166/370 |
| 6,176,312 B1 * | 1/2001 | Tubel et al. | 166/250.15 |
| 6,311,772 B1 * | 11/2001 | Myhre et al. | 166/278 |
| 6,397,949 B1 | 6/2002 | Walker et al. | 166/374 |
| 6,505,682 B2 * | 1/2003 | Brockman | 166/250.15 |
| 6,622,794 B2 * | 9/2003 | Zisk, Jr. | 166/373 |
| 6,675,891 B2 * | 1/2004 | Hailey et al. | 166/228 |
| 6,679,332 B2 * | 1/2004 | Vinegar et al. | 166/373 |
| 6,722,440 B2 * | 4/2004 | Turner et al. | 166/374 |
| 6,725,918 B2 * | 4/2004 | Gano | 166/206 |
| 6,752,207 B2 * | 6/2004 | Danos et al. | 166/278 |
| 6,782,948 B2 * | 8/2004 | Echols et al. | 166/278 |
| 6,978,840 B2 * | 12/2005 | Henderson | 166/380 |

(Continued)

FOREIGN PATENT DOCUMENTS

GB    2325949    12/1998

(Continued)

OTHER PUBLICATIONS

U.S. Appl. No. 10/220,453.

*Primary Examiner*—Hoang Dang

(57) ABSTRACT

An adjustable well screen assembly having a pipe which is connectable to a production pipe, wherein the pipe comprises a hole extending from the ID of the pipe to the OD of the pipe; a screen connected to the pipe adjacent the hole of the pipe; a valve connected to the pipe, wherein the valve controls fluid flow through the hole of the pipe; a valve motor mechanically connected to the valve, wherein the valve motor opens and closes the valve; and a valve controller communicatively connected to the valve motor, wherein the valve controller instructs the valve motor as to a configuration of the valve.

27 Claims, 12 Drawing Sheets

U.S. PATENT DOCUMENTS

| | | |
|---|---|---|
| 6,994,170 B2 * | 2/2006 | Echols ........................ 166/386 |
| 2002/0189815 A1 * | 12/2002 | Johnson et al. ............. 166/373 |
| 2003/0000709 A1 * | 1/2003 | Gano .......................... 166/380 |
| 2004/0035578 A1 * | 2/2004 | Ross et al. ............. 166/250.15 |
| 2004/0134655 A1 | 7/2004 | Richards ..................... 166/276 |
| 2004/0149435 A1 * | 8/2004 | Henderson ............. 166/250.15 |
| 2004/0251020 A1 * | 12/2004 | Smith ......................... 166/236 |

FOREIGN PATENT DOCUMENTS

| | | |
|---|---|---|
| GB | 2371578 A | 7/2002 |
| WO | 02/06593 A1 | 1/2002 |
| WO | 03/023185 A1 | 3/2003 |

* cited by examiner

SURFACE FLOW CONTROLLED VALVE AND SCREEN

This application claims the benefit of U.S. Provisional Application No. 60/458,617 filed Mar. 28, 2003, the entire disclosure of which is hereby incorporated by reference.

RELATED APPLICATIONS

This application is related to commonly assigned application WO/03/023185 A1.

FIELD OF THE INVENTION

This invention relates to an adjustable well screen assembly for controlled inflow of fluids from a hydrocarbon fluid containing formation into the production tubing of a hydrocarbon fluid production well.

The invention also relates to a hydrocarbon fluid production well, which is equipped with one or more adjustable well screen assemblies.

BACKGROUND OF THE INVENTION

The art of completing wells to exclude solids particles produced by well fluids is commonly known in the literature as gravel packing.

It is common practice in the construction of wells bored into the earth to dispose steel casing or other tubular conduits inside of the well. In some well constructions the casing is grouted into the bore by placing Portland cement in the annular space between the casing and the well bore. The casing can be deployed through the depth where the productive subterranean formation or plurality of formations is encountered below the surface. In the former the well completion is referred to those familiar with the art of well completions as open hole completions, whereas those well completions where the casing and cement is run through or past the depth of the productive formation is known to those familiar with the art of well completions as cased holes. In either case of open hole completions or cased hole completions it is well practiced art to dispose across the production formation depths sand screens, slotted pipes, or pipes with holes pre-perforated at surface into the well casing on a second continuous tube known in the literature as production tubing.

Production tubing is disposed inside of the casing extending from the surface to a depth closer to the production formation. It is often desirable to place a packer on the end of the production tubing to force well fluids up the tubing and avoid fluids being produced up the casing. The production tubing is then a removable pipe that is disposed in wells generally in jointed lengths of 40 feet (about 12 m), but can be deployed as a continuous tubing string in what is commonly known in the oil and gas industry as continuous tubing. It is common practice to deploy in production tubing string various apparatus to allow for well fluid control. It is also common to control such devices from surface using electrical and hydraulic tubes disposed simultaneously with the production tubing and connected to the outer diameter of the production tubing. These hydraulic tubes are known to those familiars with the art of well completions as control lines.

In the cased hole completions it is common practice to run explosive charges into the well after the casing is cemented across the productive formation depths and perforate holes through the casing and cement into the productive formation to create a path for fluid flow into the well.

In many wells either in cased or open hole completions unwanted formation solids are produced into the well along with the production fluids. These solids are often undesirable and many methods of stopping these solids from flowing into the well whilst producing the fluids are well defined in the literature as the art sand control. One of the more familiar methods of stopping solid flow is to perform a gravel pack.

A gravel pack is performed by placing a known size of sand, which is referred to as the gravel, into the well across the production formation to create a filter medium to stop or reduce the flow of solid materials from the formation into the well. The gravel is most commonly prohibited from flowing into the well by a device commonly know as a well screen. The well screens are designed to keep the specialized sand mesh, known as the gravel, in place in the annular space between the casing or well bore outside of the screens forming the filter media.

The current methods of placing a gravel pack is requires that the screens be deployed in the well on a tubing string from surface until the screens are at the depth of the producing formation. At this point sand is placed around the screens by various methods of pumping, circulating, and other wise dispose sand around the screens. Once the sand is placed around the screens the tubing string is detached from the screens and extracted from the well. Thereafter the production tubing with packers, control lines, sliding sleeves, and packers are disposed in the well above the screens. Hence the screens are detached from the production string in the common known methods of the industry.

It is current practice to build the well screens out of wire wrap welded to bars running parallel to the screen axis and the bars are placed around a base pipe extending the length of the screen with holes through the base pipe. This base pipe forms the structure to which the wire wrap and welded bars are attached. Hence the commonly known well screen consists of wire wrap helically wrapped around the circumference of the screen attached to welded bars that are fitted onto the outer diameter of base pipe. In other designs of sand screens the screen is manufactured with sintered materials located between. The wire wrap or in some cases outside of the wire wrap. In all cases the screen has an inner pipe base with holes or other geometric penetrations to allow fluids to flow into the screen's inner diameter.

The well screen lengths disposed in wells vary in length to accommodate the depth and heights of production zones. To accommodate deployment of screens they are run in sections and connected on surface to match the height of the production zones.

In many wells there exists in one common well bore multiple production formations that are perforated or otherwise left open hole to allow simultaneous production from several formations at varying depths into the well bore and up the production casing. Often in these multiple production formations wells the different formations in the earth are separated by lithology that does not have productive fluids often times due to lower permeability and porosity. With the current art these varying production formations are completed simultaneously and flow into a common production tubing to surface. It often occurs that one productive formation will produce less fluids, or unwanted fluids, or for resource management reasons the varying formations may be more desirably produced at different flow rates or be produced at different times. In the case of gravel packed wells the methods to shut of production from a formation in a well with multiple production formations producing simultaneously into a common well bore requires mechanical well intervention techniques known to those familiar to the art. These intervention techniques can include, squeeze cementing, the setting of plugs via wireline and rig methods, and the pulling of production tubing, control lines, electrical cable, packers, sleeves and other disposed subterranean devices in the well. The above prior art techniques require mechanical intervention into the well with pipes, wireline, or pumped chemicals into the well bore to affect the inflow of fluids into and through screen systems.

U.S. Pat. No. 5,447,201 discloses an adjustable fluid inflow assembly for an oil or gas well where the influx of fluids from a plurality of annular inflow zones is controlled by a series of annular disk shaped valves which are each arranged between a downstream end of each inflow zone and a production tubing passing there through.

A disadvantage of the known assembly is that all fluid entering an annular inflow zone needs to be discharged through an annular disk shaped valve and the fluid flow rate in each valve is therefore high which causes a high rate of wear of the valve. The current invention aims to alleviate this and other disadvantages of the known well inflow control assembly such that production formations can be shut off or their fluid production reduced from production zones by non-intervention methods from surface.

U.S. Pat. No. 6,397,949 discloses a pressure actuated valve for use in well completion assemblies. The valve is operable by pressure between three configurations. In a first configuration, the valve is in a locked-closed configuration. In a second configuration, the valve remains closed but is unlocked. In a third configuration, the valve is open. Also disclosed is a method of installing and operating a three pressure actuated valve in a well completion operation. Once this valve is opened, it requires mechanical intervention to close it.

GB 2,325,949A discloses a well screen assembly that includes sensors and multiple valves to control inflow into the screen from different sections of the wellbore.

Further, modular flow detection and flow regulations systems are currently on the market. Conventional flow detection and flow control technology is modular, and is placed inside a production zone, or well screen after the screen is installed into the well. Conventional, existing modular systems, due to their physical size and flow considerations, can place undue flow restrictions on a producer or injector well, particularly if placed within a conventional well screen. Also, existing systems would not be ideally placed to detect certain well flow phenomenon which an integral screen system could reliably detect, measure, characterize, and flow regulate.

SUMMARY OF THE INVENTION

In one embodiment, the present invention integrates the screen with the flow detection/regulation hardware. Integration enables greater through ID and net overall lengths of flow regulation devices to minimize well inflow impact of the flow devices. Also, the invention in some embodiments, places the requisite detection, characterization, and measurement devices in intimate proximity to the medium to be detected, characterized, measured, or controlled. The invention in some embodiments permits monitoring and control for each screen joint in a system having multiple screens. Also, in some embodiments, the invention provides methods to deploy integrated annulus flow control devices which control zonal flow regulation, detection, measurement, characterization, isolation, and stimulation.

The invention in some embodiments pertains to well screens incorporating flow detection, flow characterization, measurement, flow regulation and flow control. The invention contains, in some embodiments, integrated flow, i.e., these devices are built into the well screen assembly(ies). The devices may have both an active, and a passive nature. Detection, characterization, and measurement devices can send and retrieve data from both a discreet point (single point) detection type, and/or send and/or retrieve data from a distributed type of detection network (transceivers, sondes, glassfiber, etc. placed throughout the well screen). The invention can regulate or control flow, (oil, water, gas and solids such as sand or formation solids, or a mixture of these) whether that flow is inward flow (production) or outward flow (injection). The invention in some embodiments, is capable of regulating flow in varying amounts, from full "on" to full "off" and partial regulation such as "choking" or "throttling". One method to regulate flow includes a control valve either internal or external to the screen base pipe for flow control by hydraulic or electric actuation. Flow regulation through the screen may employ other controllable valve or throttling choke designs placed at distributed or discrete points along the base pipe of the screen. The invention embodies optional methods to add selective annulus flow restrictors which are integral to the sandscreen assembly, and are activated, when desired, as an integral part of the sand screen assembly and sand control process, and enhance or assist in regulation and control of the flow which can occur in the annulus outside of the well screen jacket.

Data transmission and control signals may be deployed by installing hollow tube screen ribs in place of conventional solid tube screen ribs to provide a conduit for electrical, optic fiber, or hydraulics. The hollow tube ribs could also provide hydraulic communication for selective fluid flow paths for chemical injection, stimulation, or other flow objectives.

The sandscreen may be equipped with one or more sensors for monitoring physical parameters such as the pressure, temperature, velocity and/or composition of the fluids flowing through the screen and the actuator is designed to move the sleeve between the first and second position thereof in response to signals generated by at least one of the sensors deployed in the screen system.

The invention also relates in some embodiments to a hydrocarbon fluid production well system comprising a hydrocarbon fluid inflow zone which is equipped with a plurality of axially spaced adjustable well screen assemblies with valves interconnected by blank pipe sections on which expandable packers are arranged which provides a fluid seal in the annular space between the outer surface of the blank pipe section and the inner surface of the wellbore. In such case it may be preferred that the valve of each adjustable well screen assembly may be opened and closed independently of the other valve or valves.

The present invention includes in some embodiments a method of disposing well screens into wells such that production formations fluid flows into the well can be controlled by subterranean devices disposed in the well attached to well screen systems.

The present invention provides in some embodiments an apparatus to allow for well screen system to be disposed into well bores simultaneously with production tubing, and control tubes deployed continuously from surface to the sand screen system depths. Hence this invention teaches in some embodiments the use of continuous connection of tubes and/or electrical cable from the surface to the production formations depths where the tubes are attached to sand screen systems prior to, during, and after the gravel pack operations such the tubes and screen system do not need to be disconnected from the surface deployed production tubing. One end of the control tube may extend to surface to allow communication and/or power to be transmitted to the subterranean depth where the sand screen system is disposed.

This invention apparatus then allows subterranean devices and sensors to be attached to sand screen systems such that data can be read and signals and power can be sent to the down hole system.

This invention in some embodiments allows for sand screen systems to reduce or shut off fluid flow, determine the flow characteristics and reservoir properties of down hole formations, and to isolate different production zones completed simultaneously in a common well bore.

The sandscreen assemblies of the present invention provide in some embodiments surface control of inflow and outflow at each screen joint via a single control line without mechanical intervention. This allows production operators to control an injection profile, selectively complete the well without concentric strings, perform downhole gas lift, and reduce well intervention, i.e., section unexpectedly producing sand or water breakthrough can be turned off.

According to one aspect of the invention, there is provided an adjustable well screen assembly having: a pipe which is connectable to a production pipe, wherein the pipe comprises a hole extending from the ID of the pipe to the OD of the pipe; a screen connected to the pipe adjacent the hole of the pipe; a valve connected to the pipe, wherein the valve controls fluid flow through the hole of the pipe; a valve motor mechanically connected to the valve, wherein the valve motor opens and closes the valve; and a valve controller communicatively connected to the valve motor, wherein the valve controller instructs the valve motor as to a configuration of the valve.

BRIEF DESCRIPTION OF THE DRAWINGS

The present invention is better understood by reading the following description of non-limitative embodiments with reference to the attached drawings wherein like parts of each of the several figures are identified by the same referenced characters, and which are briefly described as follows:

FIG. 13 is a cross-sectional side view of a production system positioned within a wellbore drilled into a formation. The production system has three adjustable sandscreen assemblies connected in series with packers between.

FIG. 14 is a cross-sectional side view of a production system positioned within a wellbore drilled into a formation. The production system has three adjustable sandscreen assemblies connected in series with packers between.

The appended drawings illustrate only typical embodiments of this invention and are therefore not to be considered limiting of its scope, as the invention may admit to other equally effective embodiments.

DETAILED DESCRIPTION OF THE INVENTION

Figure 1:
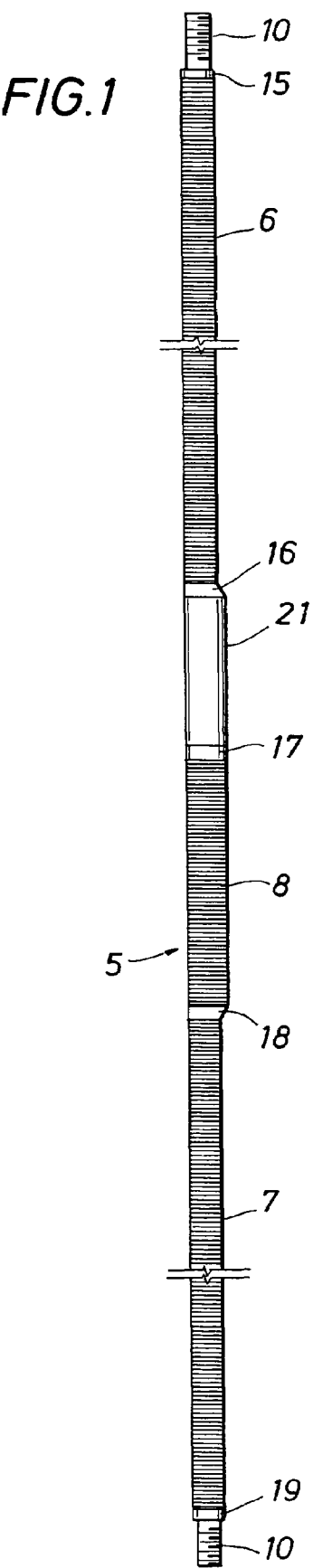
FIG. 1 is a side view of an adjustable sandscreen assembly of the present invention having an upper screen, a valve screen, and a lower screen.
Figure 3A:
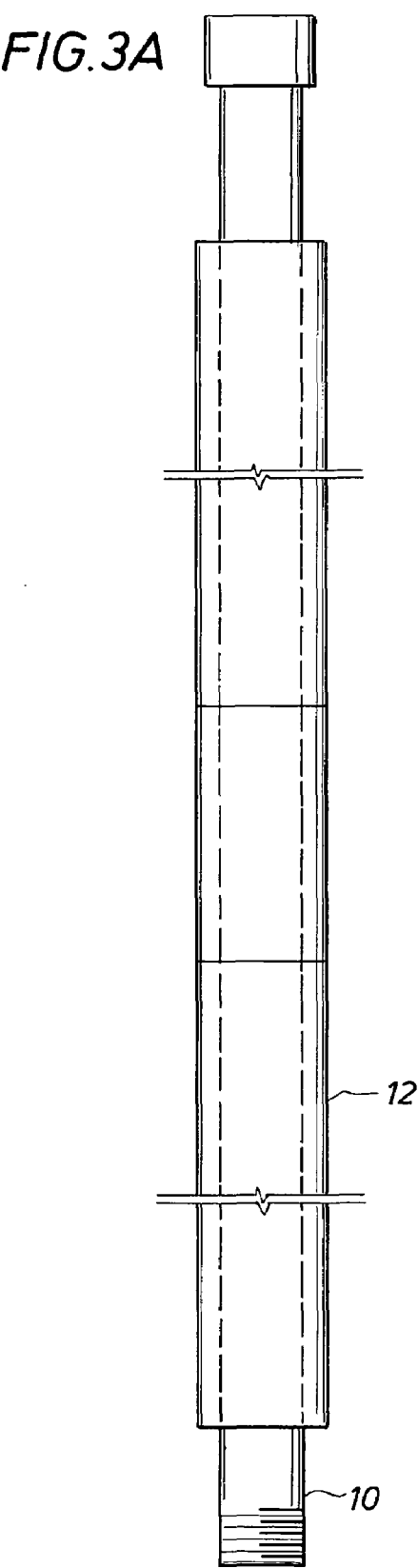
FIG. 3A illustrates a cross-sectional side view of a sandscreen used in the present invention.
Figure 3B:
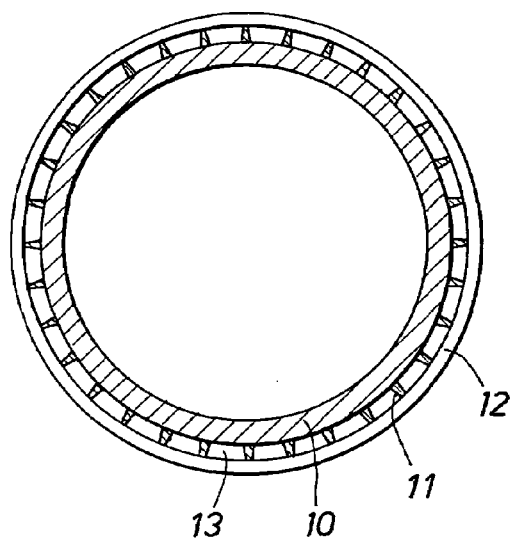
FIGS. 3B and 3C illustrate cross-sectional end views of the sandscreen shown in FIG. 3A.

Referring to FIG. 1, a side view of the adjustable well sandscreen 5 is shown. Sandscreen 5 is made up of three sections including an upper screen 6, a lower screen 7, and a valve screen 8. Each of these screens may be constructed as is known to persons of skill in the art. For example, as shown in FIG. 3B, the screens may comprise a base pipe 10, longitudinal ribs 11 and a screen 12. In this particular invention, the base pipe 10 has no holes through which fluid may flow between the exterior and interior of the base pipe 10. In this regard, the base pipe 10 is different from production screens known generally in the industry. The longitudinal ribs 11 are positioned in the longitudinal direction about the exterior of the base pipe 10. The screen 12 is then wrapped around the longitudinal ribs 11 so that passages 13 are defined between the base pipe 10, adjacent longitudinal ribs 11, and the screen 12. The passages 13 are volumes between the base pipe and the screen sections through which fluids flow to a valve after having passed through the screen sections. By controlling the flow of fluids through the screen sections downstream of the screen sections, the whole surface area of the screen can be utilized for the full operating range of the screen. Sandscreens that limit flow through the screen by blocking off portions of openings in the screens will cause greater velocities through the remainder of the screen as flow area is limited. Higher velocities in the through the screens, and the formations adjacent to those portions of the screen sections is not desirable, and could increase sand entrainment in the fluids flowing through the screen sections. The present invention therefore can decrease flow through the screen and also thereby reduce velocity through the screen, which may decrease coning of water and entrainment of solids. In one embodiment of the present invention, the pressure drop through the screen section is greater than the pressure drop through the volume between the screen section and the valve so that fluid will flow through the whole screen section area more evenly as opposed to flowing more through the portion of the screen section closest to the valve.

Figure 2:
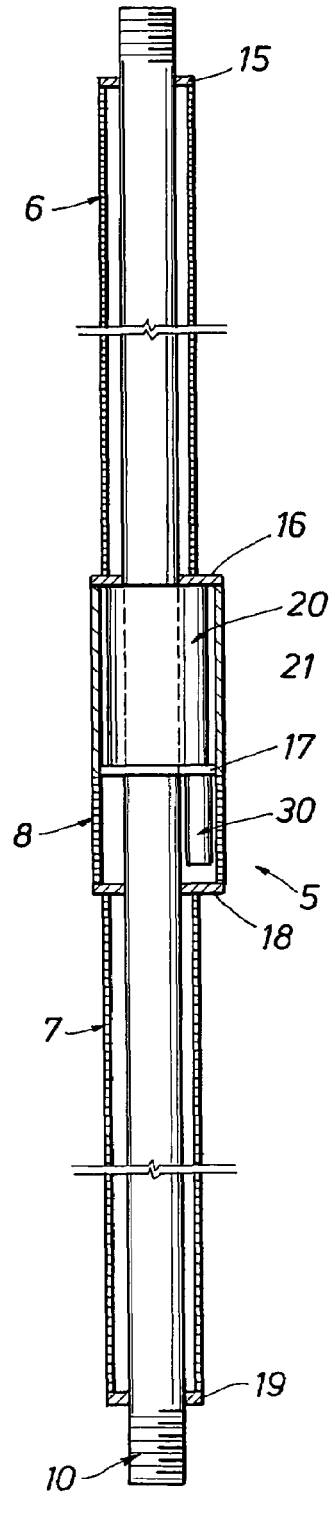
FIG. 2 is a cross-sectional side view of an adjustable sandscreen assembly having an upper screen, a valve screen, and a lower screen, wherein an electronic pod and a valve pod are shown inside the valve screen.

Referring to FIG. 2, an abstract cross-sectional side view of the adjustable sandscreen 5 is shown. The base pipe 10 runs the entire length of the system. Upper screen 6 and lower screen 7 are attached concentrically about the base pipe 10. The valve screen 8 is concentric about the base pipe 10 in a middle section of the base pipe. The outside diameter of the valve screen 8 is relatively larger than the upper and lower screens 6 and 7. An electronics POD 20 and valve 30 are positioned in the annulus between the base pipe 10 and the valve screen 8. This design minimizes the total length of the blank pipe 10 by placing the valve 30 in the middle of the assembly and using screen at varying diameters to cover the tubing as well as a portion of the POD.

Referring again to FIG. 1, the base pipe 10 extends the entire length of the assembly. An upper screen transition piece 15 connects the end of the upper screen 6 to the base pipe 10. An upper valve transition piece 16 is positioned between the opposite end of upper screen 6 and the upper end of a POD housing 21. The POD housing 21 is connected to a middle valve transition piece 17, which in turn is connected to an upper end of the valve screen 8. A lower valve transition piece 18 is connected between the valve screen 8 and the lower screen 7. A lower screen transition piece 19 is connected between the lower screen 7 and the base pipe 10.

Figure 3C:
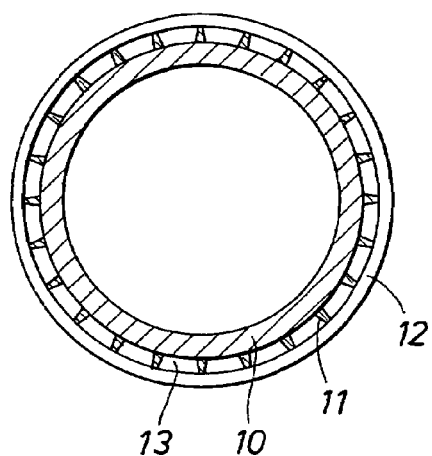

According to one embodiment of the invention, the upper and lower screen 6 and 7 may be 3.5 inches in diameter and approximately 10 feet in length. The valve screen 8 may be about 5 inches in diameter and approximately 4 feet long. The POD housing 21 has an outside diameter similar to the valve screen 8 and may be approximately 2 feet in length. The base pipe may be about 30 feet long in this embodiment. Any screen known to persons of ordinary skill in the art may be used with this invention. For example, as shown in FIGS. 3A through 3C, a wire wrap screen 12 is wrapped around longitudinal ribs 11 positioned on the exterior of a base pipe 10. Alternatively, a slotted base pipe may also be used.

Figure 4A:
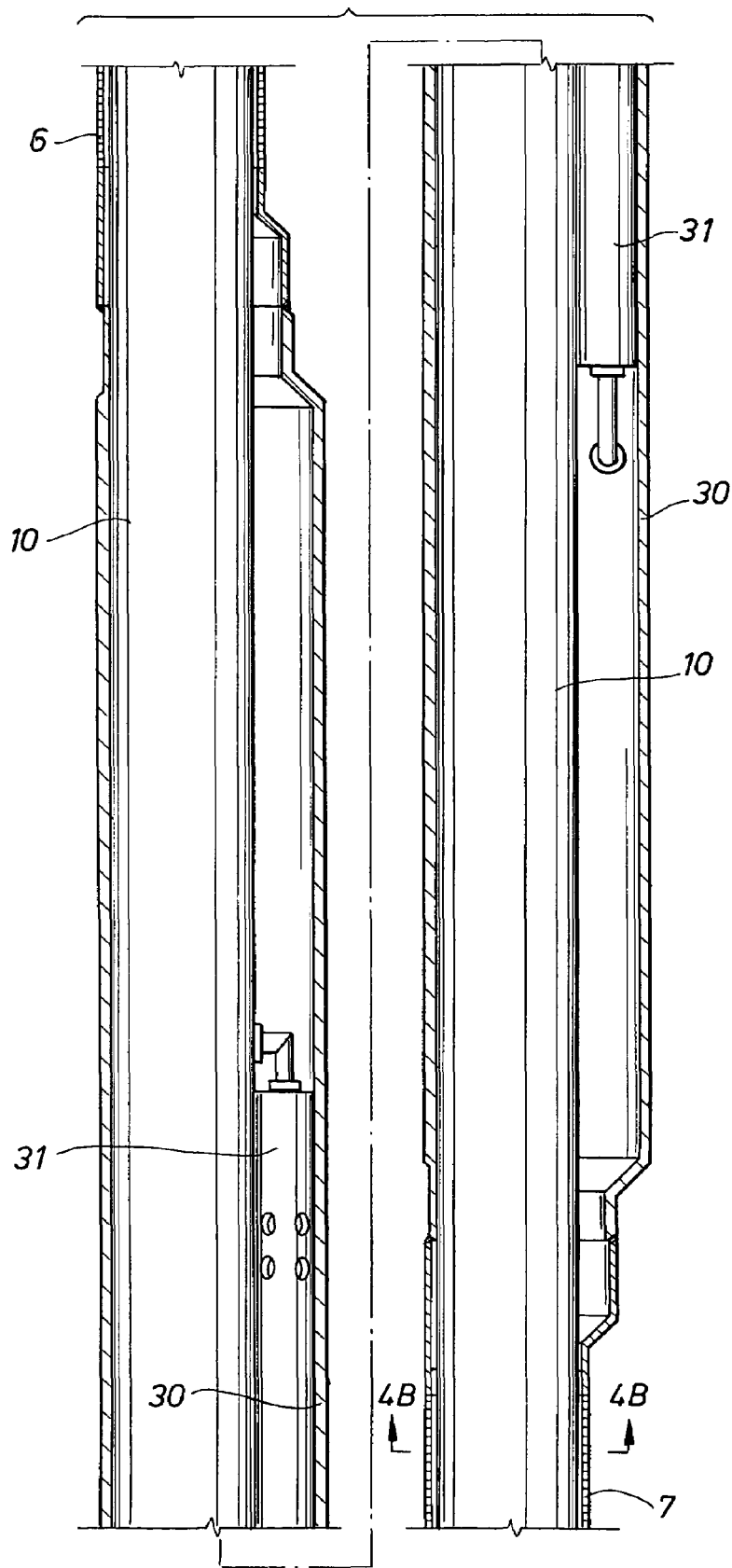
FIG. 4A shows a cross-sectional side view of the valve pod with the upper and lower screens attached to the ends thereof.
Figure 4B:
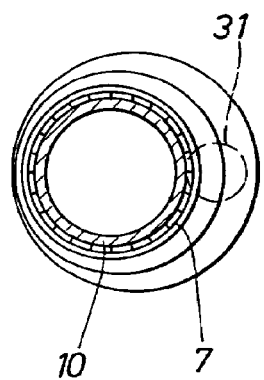
FIG. 4B shows an end view of the valve pod and lower screen shown in FIG. 4A.

Referring to FIGS. 4A and 4B, a side view and an end view of the adjustable sandscreen is shown, respectively. A base pipe 10 extends the length of the assembly. Upper screen 6 and lower screen 7 are attached to the base pipe. The assembly also has a valve POD 30 with a valve 31 inside. The valve 31 resides in a chamber defined between the base pipe 10 and the valve POD housing 30.

Figure 5A:
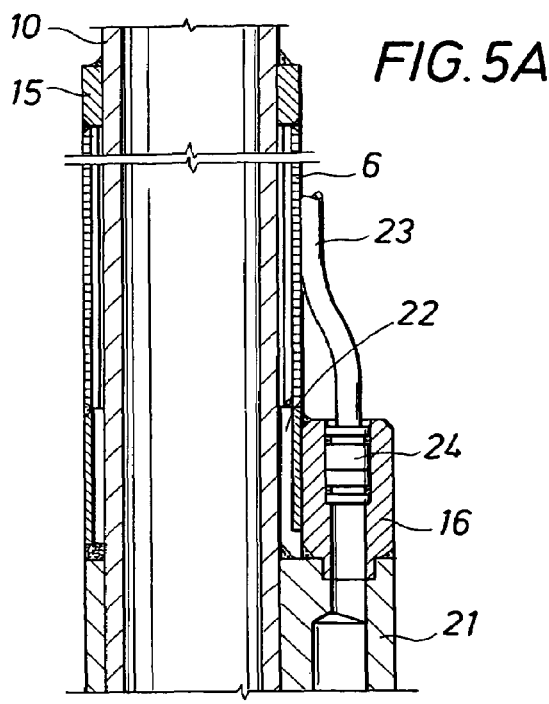
FIG. 5A is a cross-sectional side view of the lower screen, the upper valve transition piece, and a portion of the electronics pod housing.

FIG. 5A illustrates a cross-sectional side view of the upper screen 6 and upper valve transition piece 16. The upper valve transition piece 16 forms a seal which connects the upper screen 6 to the electronics POD housing 21. The inside diameter of the upper valve transition piece 16 is larger than the outside diameter of the base pipe 10, so that a transition passage 22 is there between defined. Electric cable 23 is connected to the upper valve transition piece 16 by an electric connector 24.

Figure 5B:
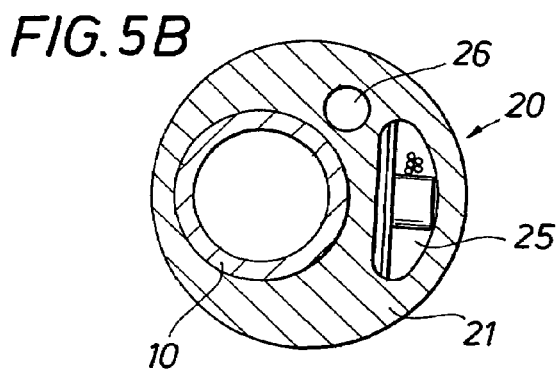
FIG. 5B shows a cross-sectional end view of the electronics pod housing.

Referring to FIG. 5B, a cross-sectional end view of the electronics POD housing 21 is shown. The electronics POD housing 21 has a solid construction with holes there through. The base pipe 10 extends through the largest hole herein. A vacuum chamber 25 extends axially through the electronics POD housing 21. The vacuum chamber 25 is an air-tight vacuum chamber in which electronic components reside. A conduit 26 also extends axially through the POD housing 21. The face of the upper valve transition piece 16, which mates with the electronics POD housing 21 is somewhat conical in shape so as to define a pooling reservoir for fluid flowing through the upper screen 6. In particular, fluid flows through the wire wrap screen 6, into passages 13 between the longitudinal ribs 11, into the transition passage 22, until it pools in the pooling reservoir between upper valve transition piece 16 and electronic POD housing 21. Fluid collected in the pooling reservoir passes through the electronics POD housing 21 by conduit 26.

Figure 5C:
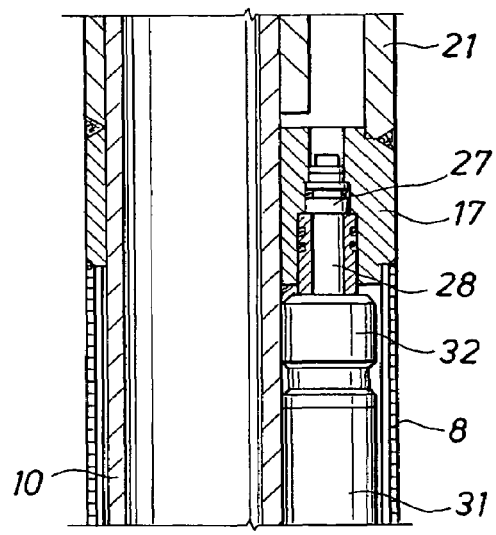
FIG. 5C illustrates a cross-sectional side view of a portion of the electronics pod housing, the middle valve transition piece, the valve and the valve screen.

Referring to FIG. 5C, a cross-sectional side view of the middle valve transition piece 17 is shown. The middle valve transition piece 17 connects on one side to the electronics POD housing 21 and on the other side to the valve screen 8. The middle valve transition piece 17 comprises a electric connector 27. The electrical cable (not shown) extends between the electric connector 24 in the upper valve transition piece 16 to the electric connector 27 in the middle valve transition piece 17. The valve motor assembly 32 is connected to the middle valve transition piece 17 by plug 28, wherein the plug 28 mates electrically with the electric connector 27. The conduit 26 (not shown) also extends through the middle valve transition piece 17 in an axial direction.

Figure 5D:
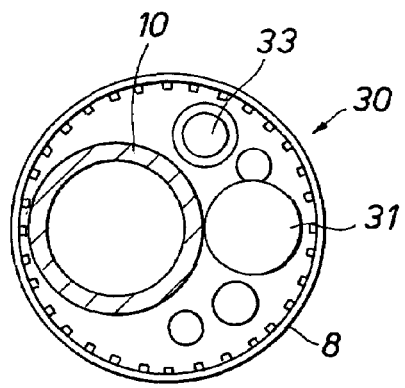
FIG. 5D shows a cross-sectional end view of the valve pod with the base pipe and valve extending therethrough.

FIG. 5D illustrates a cross-sectional end view of the valve POD 30. The base pipe 10 extends axially through the valve POD 30. The valve screen 8 defines the outer circumference. The valve 31 also extends axially in the space between base pipe 10 and the valve screen 8. An electric cable 33 also extends axially through the valve POD 30.

Figure 5E:
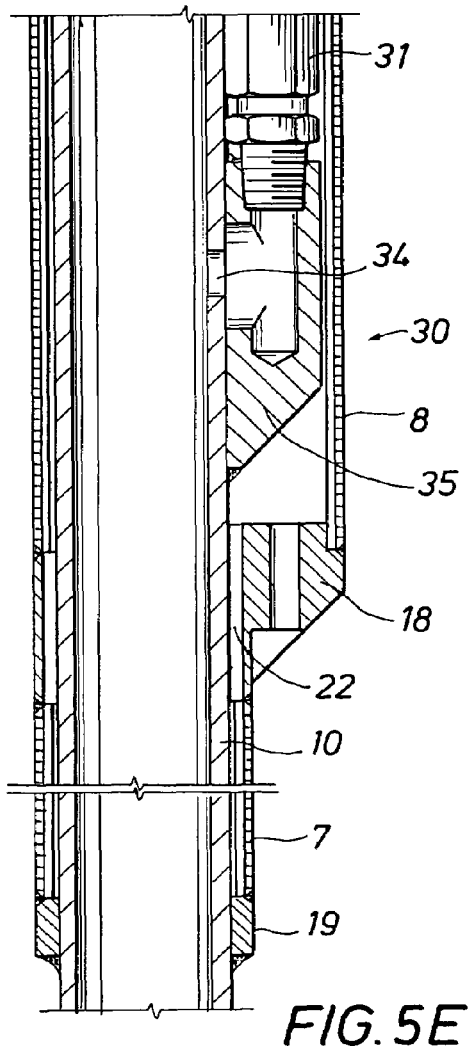
FIG. 5E shows a cross-sectional side view of the valve pod, the lower valve transition piece and the lower screen.

FIG. 5E is a cross-sectional side view of the lower valve transition piece 18 and the lower screen transition piece 19. As with the other components, the base pipe 10 extends through this portion of the assembly as well. The lower screen 7 is attached to the outside diameter of the base pipe and the outside of the valve POD 30 is defined by the valve screen 8. Within the valve pipe 30, a base port 34 extends through the wall of the base pipe 10. A port block 35 is sealably connected to the outside diameter of the base pipe 10 so as to encircle the base port 34. The valve 31, shown in FIG. 5D, is threadably connected to the port block 35. Thus, the port block 35 provides a fluid conduit between the valve 31 and the inside diameter of the base pipe 10.

Fluid on the exterior of the lower screen 7 is communicated to the inside diameter of the base pipe 10 by flowing through the lower screen 7, through passages 13 between longitudinal ribs and into a transition passage 22 between the lower valve transition piece 18 and the base pipe 10. From the transition passage 22, the fluid flows into the interior of the valve POD 30 where it is able to communicate with the valve 31. If the valve 31 is open, the fluid is allowed to flow through the valve 31, into the port block 35, through the base port 34 and into the inside diameter of the base pipe 10. Similarly, fluid on the exterior of the valve screen 8 is allowed to communicate with the inside diameter of the base pipe by flowing through the valve screen 8 and into the interior of the valve POD 30 where it communicates directly with the valve 31. It thereafter follows a path into the base pipe 10 through the port block 35 as just described.

Figure 6A:
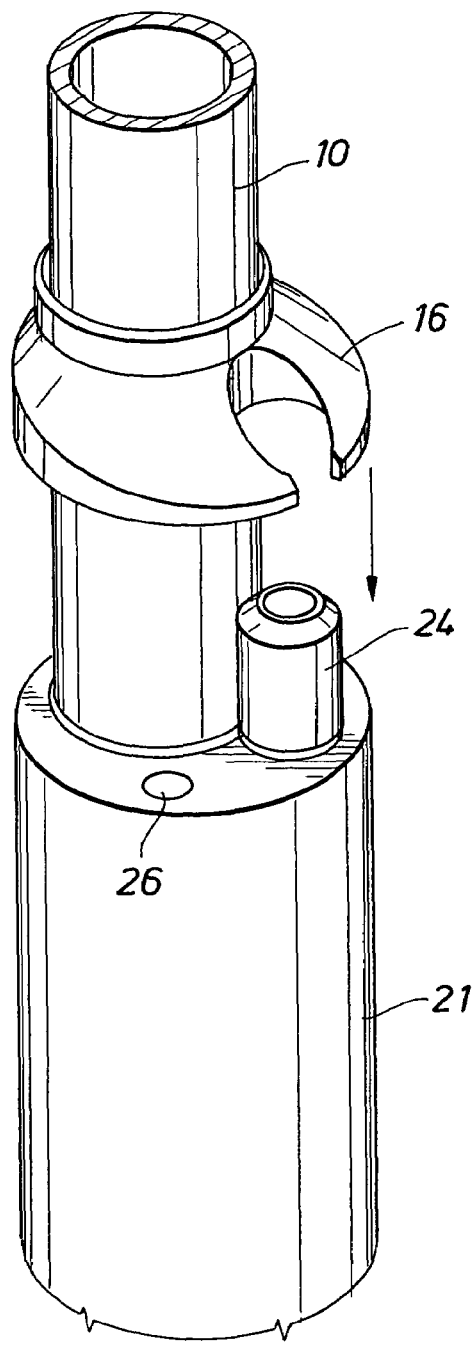
FIGS. 6A and 6B illustrate perspective views of the upper valve transition piece and a portion of the electronics pod housing in disassembled and assembled configurations, respectively.
Figure 6B:
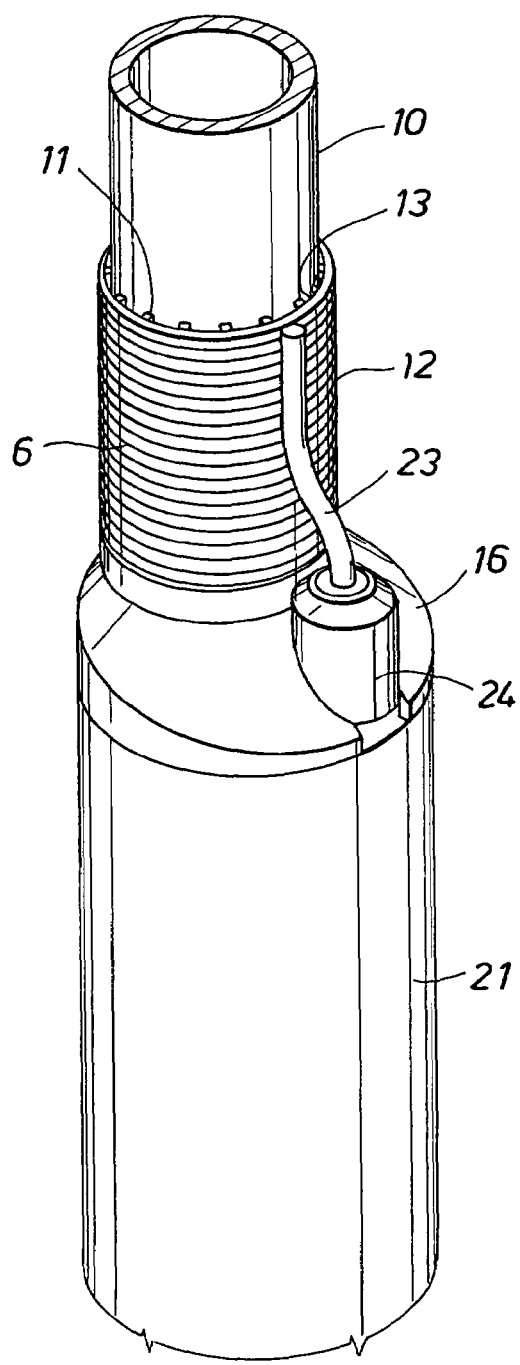

FIGS. 6A and 6B illustrate perspective views of the upper valve transition piece 16 in disassembled and assembled configurations, respectively. Once the electronics POD housing 21 is attached to the base pipe 10, the upper valve transition piece 16 is mated with the POD housing 21. After the upper valve transition piece 16 is attached, upper screen 6 is mounted to the base pipe 10 and electric cable 23 is plugged into the electric connector 24.

Figure 7A:
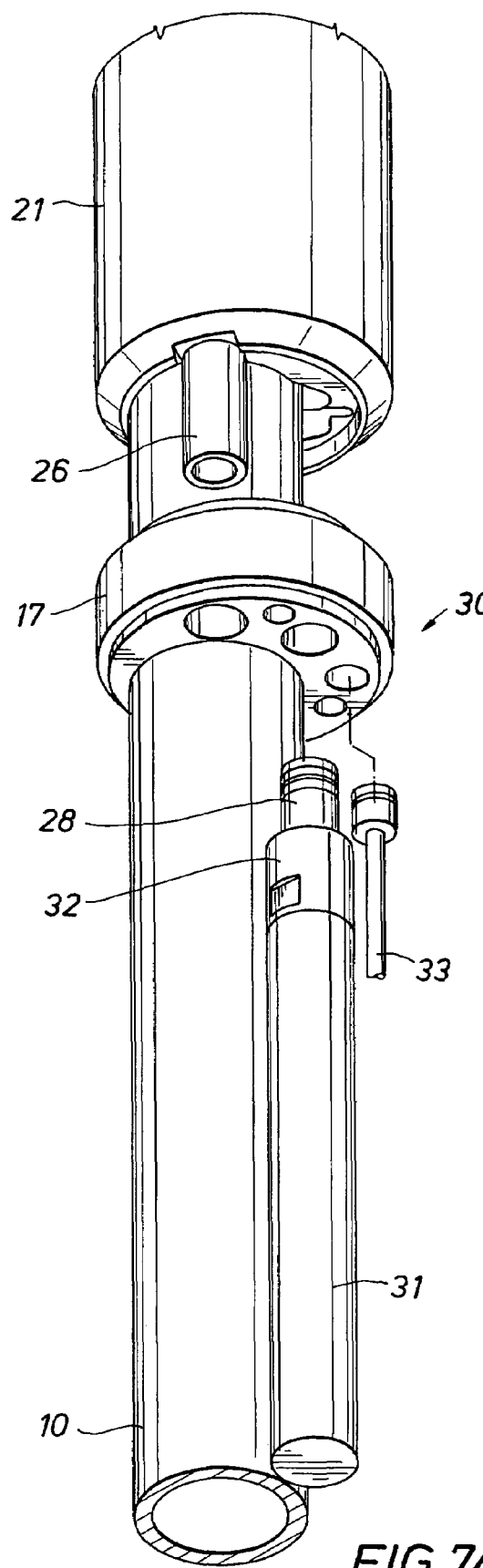
FIGS. 7A and 7B illustrate perspective views of the electronics pod housing, the middle valve transition piece, the valve pod with the valve inside, the lower valve transition piece and the lower screen, in disassembled and assembled configurations, respectively.
Figure 7B:
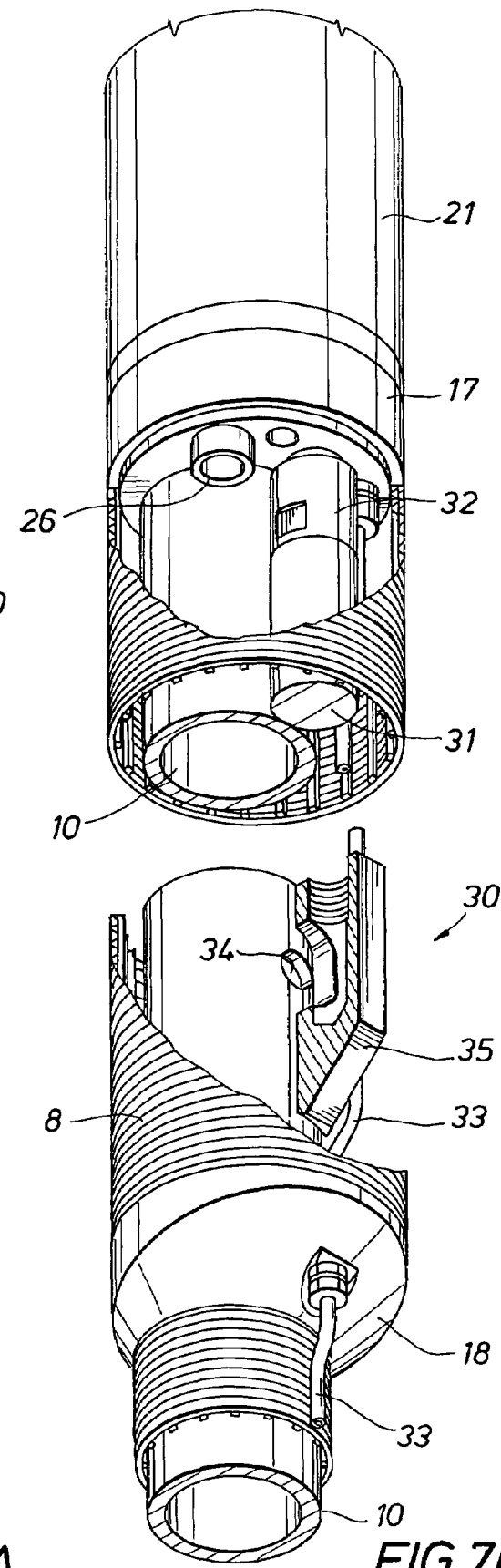

Referring to FIGS. 7A and 7B, perspective views of the valve POD 30 are shown in disassembled and assembled configurations, respectively. The valve 31 is threadably connected to the port block 35. Thereafter, a middle valve transition piece 17 slides in the direction of the valve 31 to mate with the plug 28 at the distal end of the valve motor assembly 32 with the middle valve transition piece 17 in position, the electronics POD housing 21 slides toward and mates with the middle valve transition piece 17. As previously described, the conduit 26 extends through both the POD housing 21 and the middle valve transition piece 17. In embodiments of the invention where several sandscreen assemblies 5 are to be connected in series, an electric cable 33 is also coupled to the middle valve transition piece 17. This electric cable 33 extends from one end of the valve POD 30 to the other, where it exits through a hole in the lower valve transition piece 18. As previously described, the valve POD 30 has a valve screen 8 which may comprise a wire wrap screen, a slotted base pipe, or any other screen assembly known to persons of skill in the art.

Figure 8:
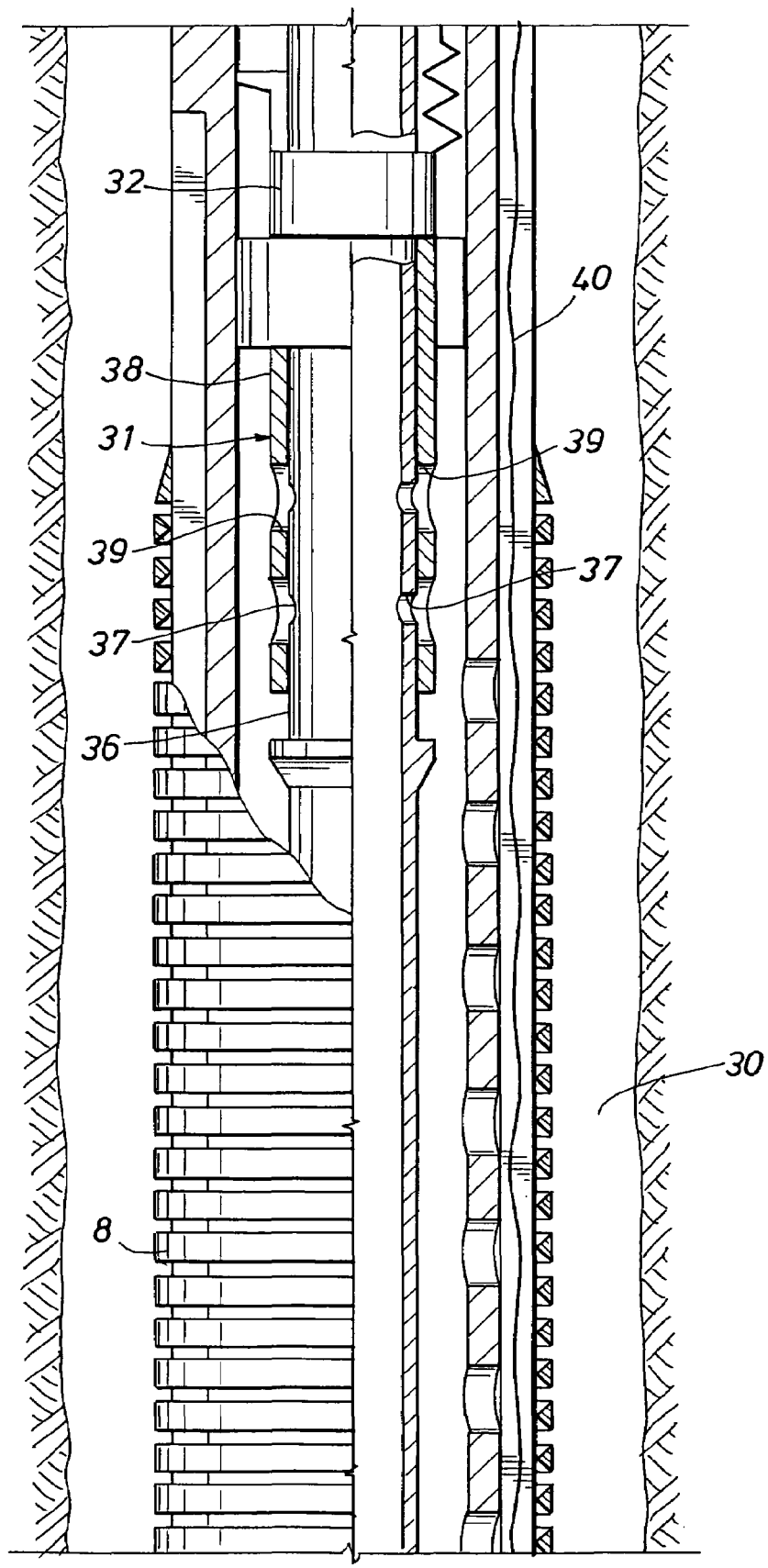
FIG. 8 illustrates a cross-sectional side view of the valve pod with the valve shown in an open configuration.

Referring to FIG. 8, a cross-sectional side view of the valve pod 30 is shown, wherein the sandscreen assembly is positioned within a wellbore. The valve screen 8 is shown partially cut away so as to reveal the valve 31 inside. The valve 31 has a valve tube 36 with several tube holes 37 extending through the wall of the valve tube 36. The valve 31 also has a valve sleeve 38 which is concentric about the outside diameter of the valve tube 36. The valve sleeve 38 has sleeve holes 39 extending through the wall of the valve sleeve 38. In FIG. 8, the valve 31 is shown in an open configuration, wherein the valve sleeve 38 is positioned relative to the valve tube 36 such that the sleeve holes 39 coincide with the tube holes 37. In the open configuration, fluid on the outside of the valve 31 flows freely through the sleeve holes 39, and the tube holes 37 to enter the inside diameter of the valve tube 36. In FIG. 8, a valve motor assembly 32 is shown for reconfiguring the valve 31. A fiber optics cable 40 is shown just inside the valve screen 8.

Figure 9:
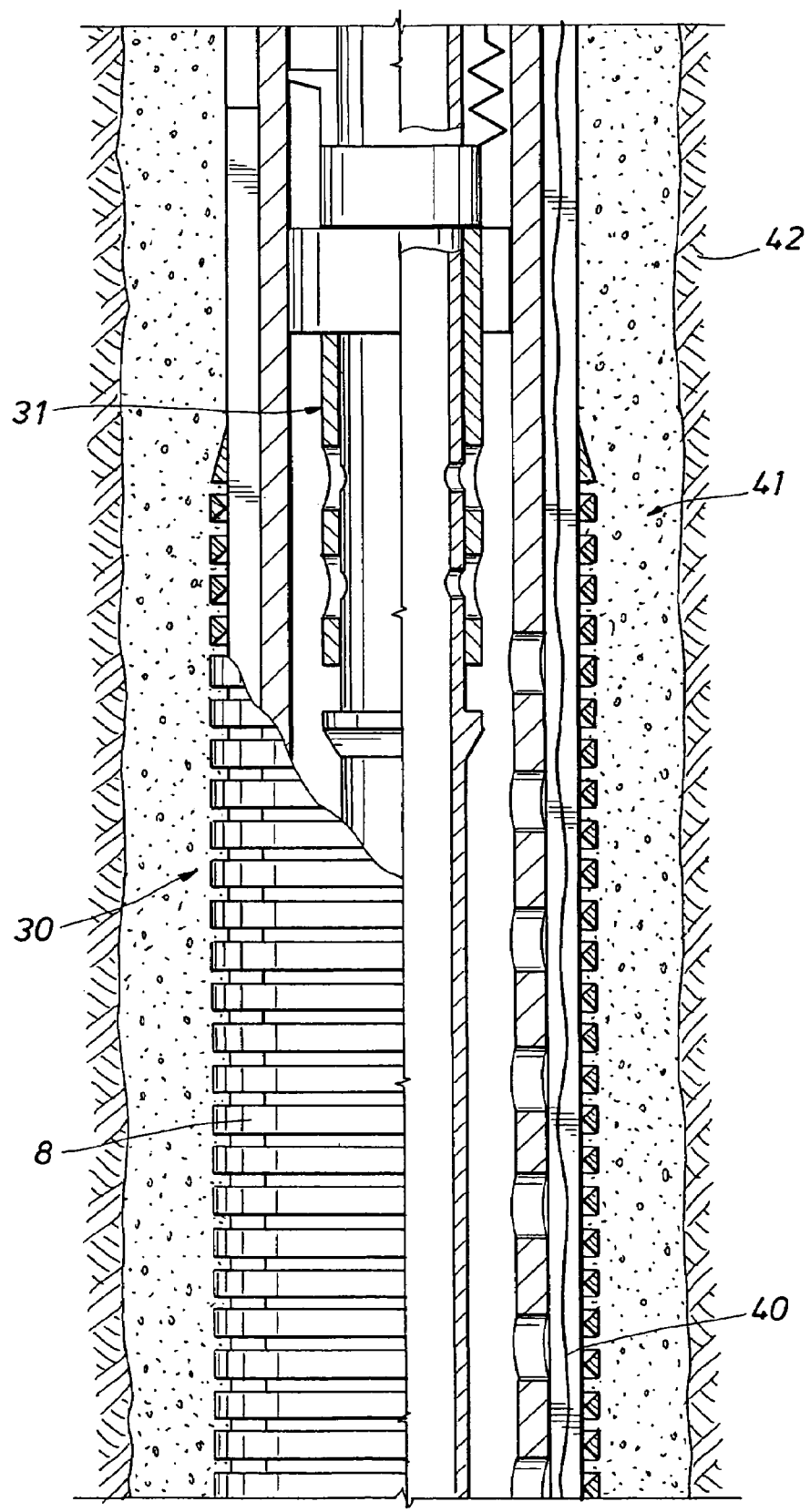
FIG. 9 illustrates a cross-sectional side view of the valve pod of FIG. 8 wherein the valve pod is gravel packed in the wellbore.

Referring to FIG. 9, the valve pod 30 of the sandscreen 5 shown in FIG. 8, is now shown with a gravel pack 41 in the annulus between the valve pod 30, and the formation 42. With the valve 31 in the open configuration, the sandscreen 5 may be gravel packed by flowing a slurry of particles into the wellbore annulus and returning the particle suspension fluid through the upper, lower, and valve screens 6, 7 and 8.

Figure 10:
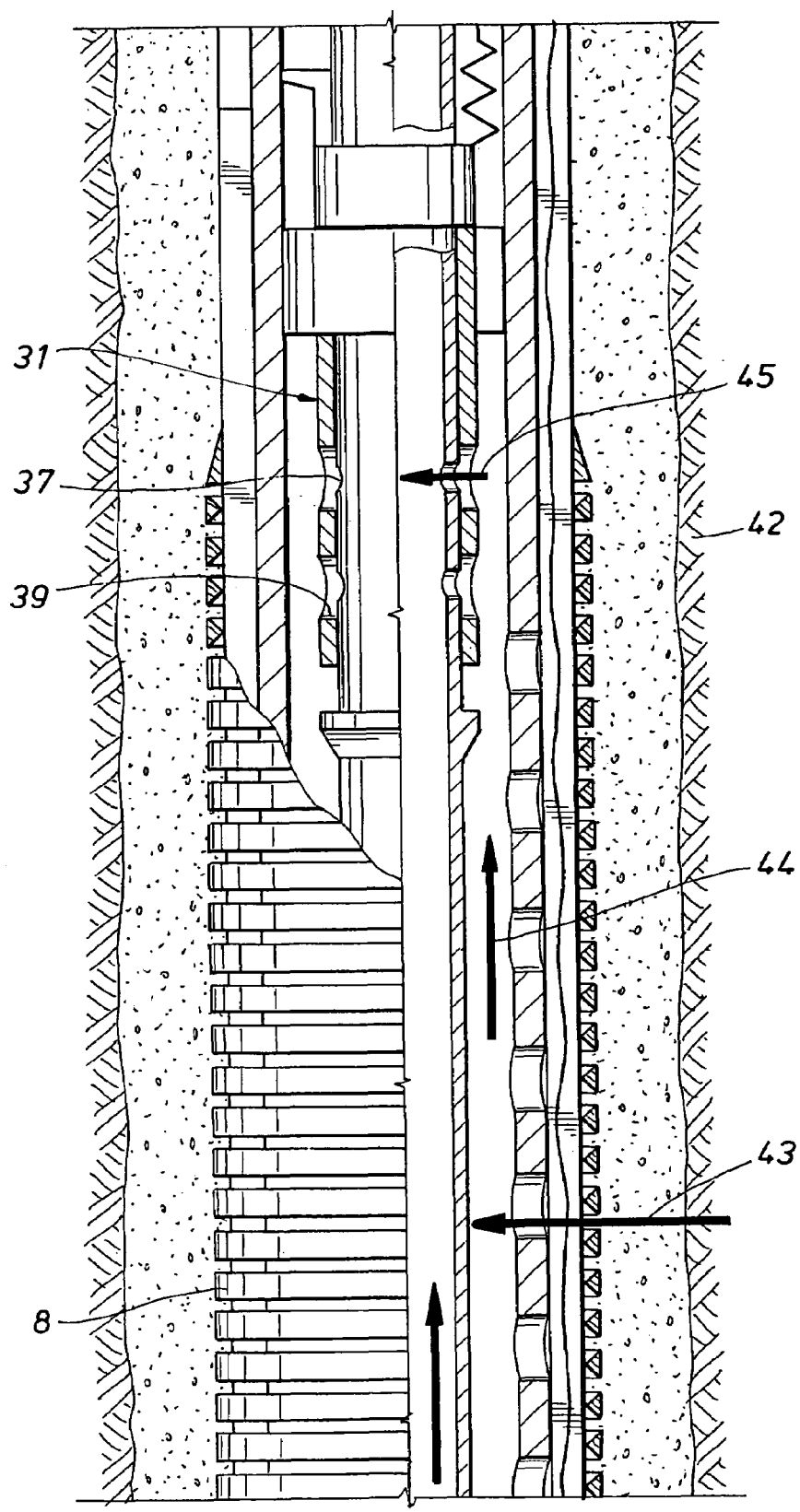
FIG. 10 is a cross-sectional side view of the valve pod shown in FIGS. 8 and 9 wherein fluid flow paths are indicated.

FIG. 10 is a cross-sectional side view of the valve pod 30 shown in FIGS. 8 and 9. Fluid flows into the valve pod 30 from the formation 42 through the valve screen 8 as indicated by arrow 43. Once fluid has entered the inside diameter of the valve screen 8, the fluid flows in an axial direction toward valve 31 as indicated by arrow 44. Formation fluids then flow into the open valve 31 through sleeve holes 39 and tube holes 37 as indicated by arrow 45.

Figure 11:
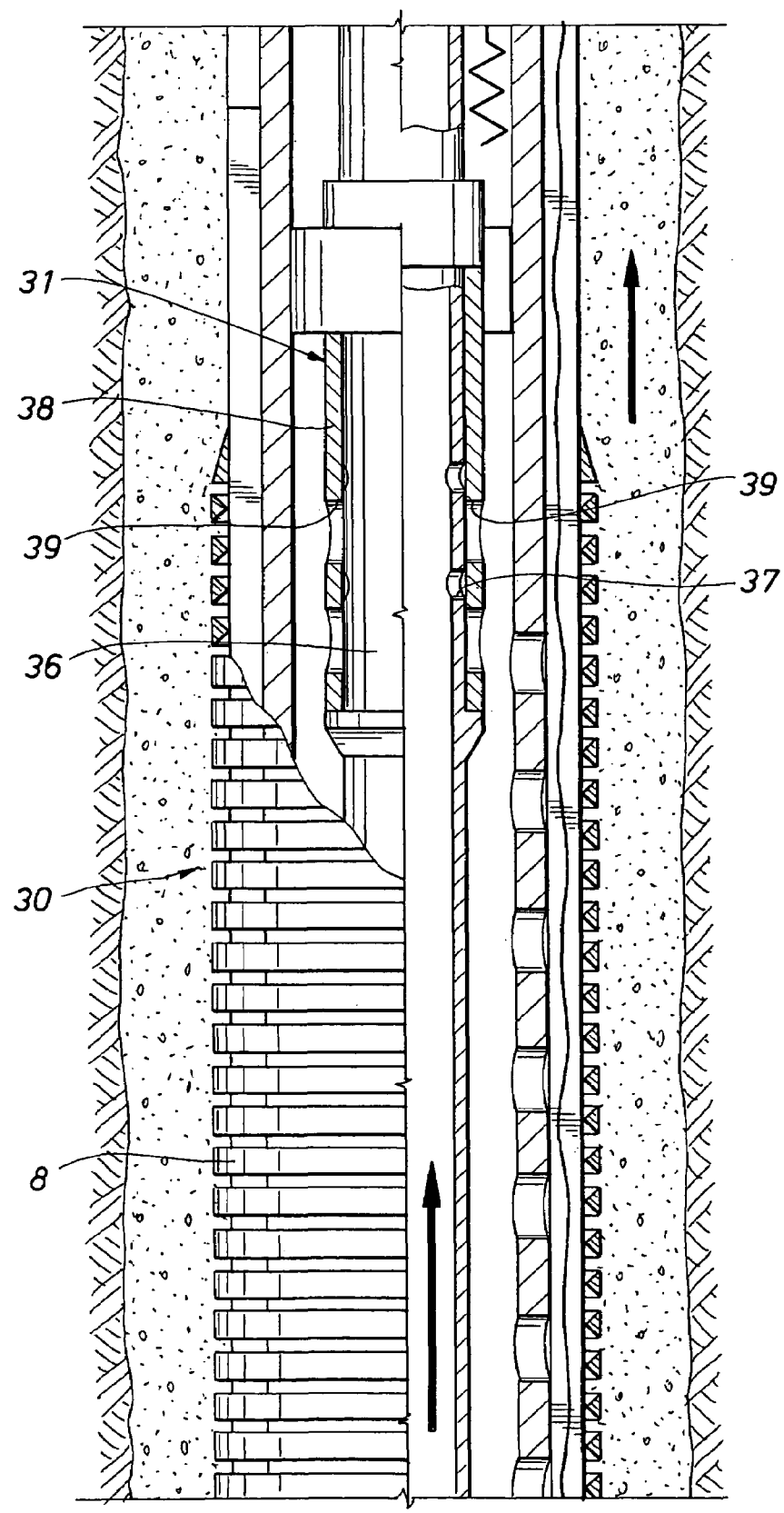
FIG. 11 is a cross-sectional side view of the valve pod shown in FIGS. 8 through 10 wherein the valve is shown in a closed configuration.

FIG. 11 illustrates the valve pod 30 shown in FIGS. 8–10. In this view however, the valve 31 is shown in a closed configuration. In particular, the valve sleeve 38 has translated axially relative to the valve tube 36. In this position, the sleeve holes 39 no longer coincide with the tube holes 37. Thus, the walls of the valve sleeve 38 close the tube holes 37 so that no fluid may flow through the valve 31.

In an alternative embodiment of the valve 31, the valve sleeve 38 does not comprise sleeve holes. Rather, the valve sleeve 38 has a uniformly solid annular wall. As before, to close the valve, the valve sleeve simply slides or translates relative to the valve tube so that the valve sleeve covers the tube holes 37. To open the valve 31, the valve sleeve 38 simply translates a sufficient distance until the entire valve sleeve has moved off of the tube holes 37.

When the valve 31 is closed, the gravel pack sandscreen completely isolates the formation. Formation fluid is not allowed to flow freely through the sandscreens and into the base pipe for production. Also, annular flow up the wellbore is significantly impeded by the gravel pack in the annulus between the sandscreen and the formation.

Figure 12:
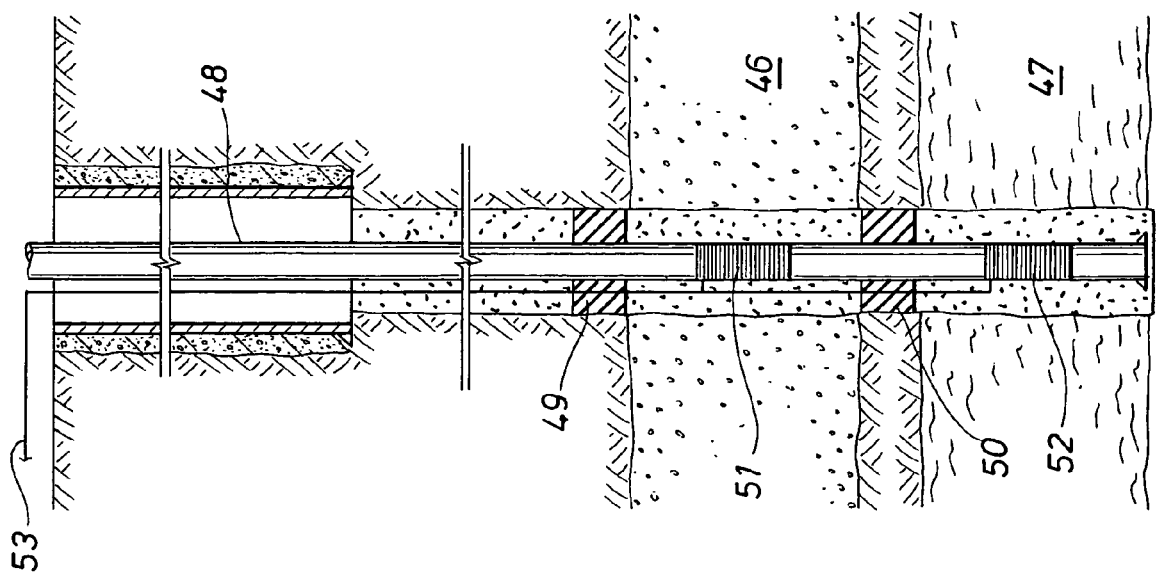
FIG. 12 is a cross-sectional side view of a production system placed in a wellbore drilled through gas and oil zones. The production system has two adjustable sandscreen assemblies connected in series.

Referring to FIG. 12, a cross-sectional side view of a wellbore is shown. The wellbore is shown drilled into a gas zone 46 and an oil zone 47. The production tube 48 is equipped with an upper packer 49, an upper sandscreen assembly 51, a middle packer 50, and a lower sandscreen assembly 52. By shutting off a section of screen, a single zone can be produced without the use of a concentric string. If the upper zone is gas, one can also use the sandscreen assembly for natural gas lift applications. The sandscreen assemblies monitoring capabilities become particularly valuable in this case. Thus, because the upper and lower sandscreen assemblies 51 and 52 may be opened and closed independently via the control line 53, the operator may selectively produce from the gas zone 46, the oil zone 47, both zones simultaneously, or neither of the zones.

Figure 13:
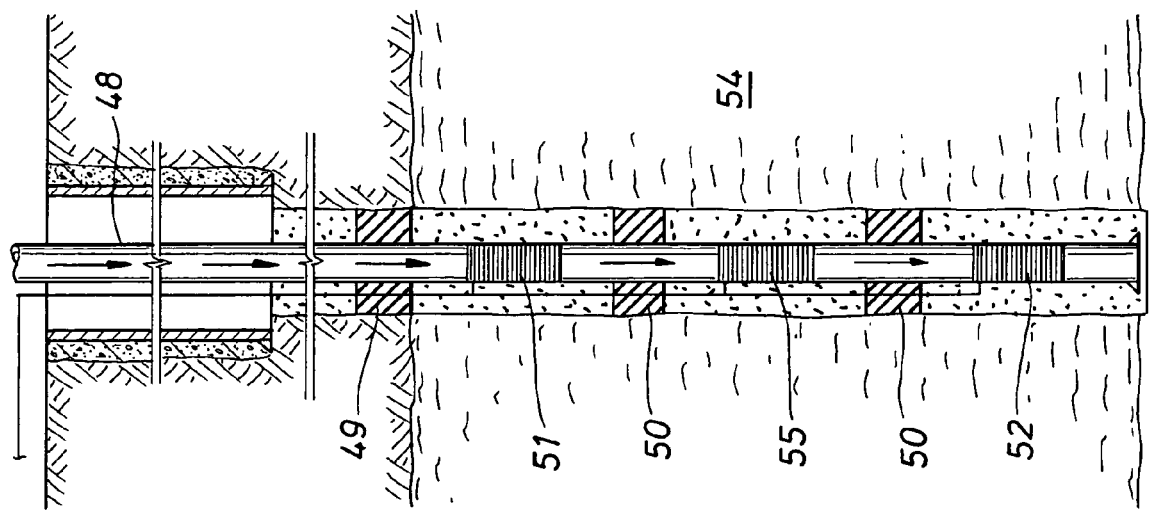

FIG. 13 illustrates a side view of a wellbore drilled into a formation 54. The production tube 48 is equipped with an upper packer 49, an upper sandscreen assembly 51, a middle packer 50, a middle sandscreen assembly 55, another middle packer 50, and a lower sandscreen assembly 52. The system shown in FIG. 13 illustrates a configuration for which an operator can control the location of water injection. For example, the operator may close sandscreen assemblies 51 and 52 and open sandscreen assembly 55. The operator may then pump water down the production tube 48 so as to inject or flood water into the formation proximate sandscreen assembly 55. Because the sandscreen assemblies 51, 55, and 52, may be opened and closed according to the operator's control, water may be injected into the formation proximate a single sandscreen assembly simply by reconfiguring the sandscreen assemblies to be opened or closed as is appropriate.

Figure 14:
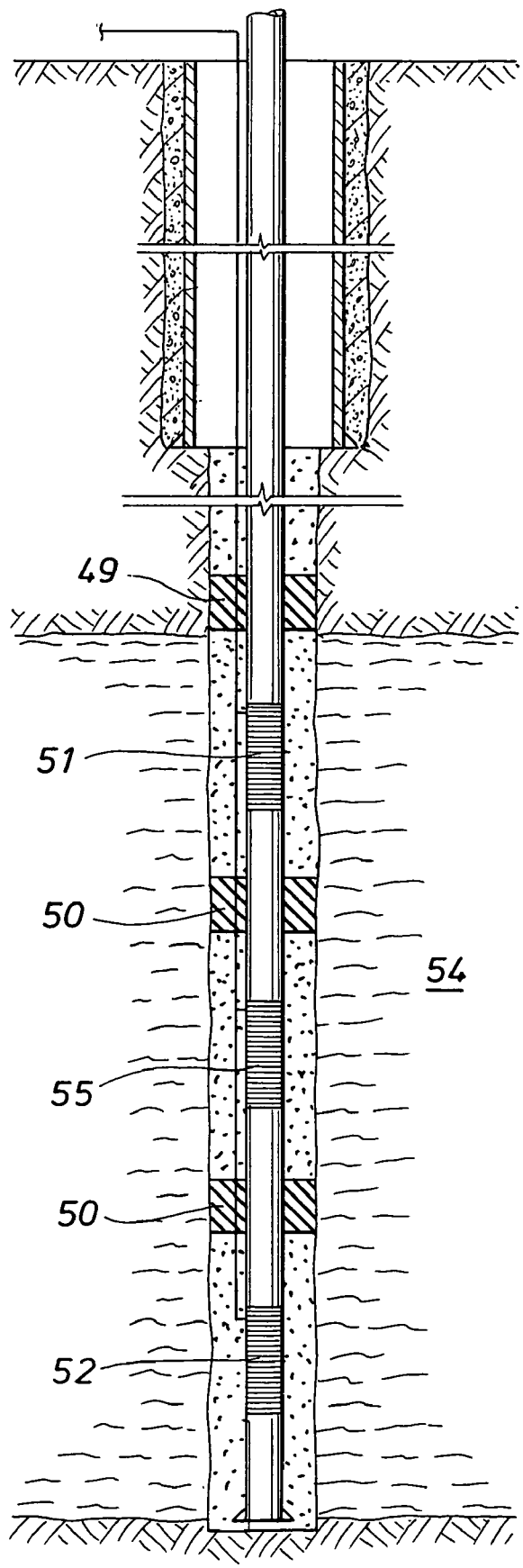

FIG. 14 is a side view of a wellbore drilled into a formation wherein the wellbore contains a production system similar to that shown in FIG. 13. In this illustration, however, a sand control failure is assumed to have occurred proximate lower sandscreen assembly 52. In a producing well that experiences a sand control failure specific to a certain section, the operator may use the sandscreen assemblies to shut off the problem section and continue producing without mechanical intervention. In particular, as shown in FIG. 14, the operator may close lower screen assembly 52 while the upper sandscreen assembly 51 and the middle sandscreen assembly 55 remains open. Thus, while lower sandscreen assembly 52 is closed due to the sand control failure, production from the formation may still be obtained through sandscreen assemblies 51 and 55.

The adjustable well screen assembly according to the invention may comprise any suitable combination of electrical power, hydraulic power, or optic powered apparatus that allow communication of power to, and transmission of data from, the assembly. If hydraulic power is used, the valve 31 is actuated from surface with hydraulic pressure supplied from surface through a hydraulic conduit. If electrical power is used, the valve 31 is actuated from surface with electric power supplied from surface through an electric cable. If optical power is used, the valve 31 is actuated from surface with optic power supplied from surface through a fiber optic cable. Pressure, temperature, velocity, composition and/or other sensors may be deployed in or around the sandscreen to indicate the flow, fluid, and pressure changes resulting from the varying sleeve position and the sensors transmit data to surface via one or more fiber optical and/or electrical signal transmission conduits attached to the screen assembly. As known to persons of skill in the art, communication and power to the screen can be achieved by electrical optical, electromagnetic and or acoustic power and signal transmission methods. Hence the invention teaches the use of multiple power and communication, methods to be used in the invention for both communications with the sensors, and to power the subterranean devices.

While the invention has been illustrated and described in detail in the drawings and foregoing description, the same is to be considered as illustrative and not restrictive in character, it being understood that only exemplary embodiments has been shown and described and that all changes and modifications that come within the spirit of the invention are desired to be protected.

We claim:

1. A method for controlling flow through a formation and a pipe within a formation, the process comprising the steps of:
   providing a base pipe having an upper end and a lower end;
   providing an upper screen attached concentrically around the upper end of the base pipe;
   providing a lower screen attached concentrically around the lower end of the base pipe;
   providing a valve located between the upper screen and the lower screen; and
   providing a valve screen attached concentrically around the valve, wherein the diameter the valve screen is greater than the diameter of the upper screen and the lower screen;
   providing a valve motor mechanically connected to said valve, wherein said valve motor opens and closes said valve; and
   providing a valve controller communicatively connected to said valve motor, wherein said valve controller instructs the valve motor as to a configuration of the valve.

2. The method of claim 1 wherein the controller is operatively associated with the valve by an electrical cable.

3. The method of claim 1 wherein the controller is operatively associated with the valve by an optical fiber.

4. The method of claim 1 wherein the controller is operatively associated with the valve by a hydraulic cable.

5. The method of claim 1 wherein the controller is operatively associated with the valve by a pneumatic cable.

6. The method of claim 1 further comprising the step of providing a data sensor communicatively connected to the upper screen or the lower screen.

7. The method of claim 1 further comprising providing a data transmitter communicatively connected to the upper screen or the lower screen.

8. The method of claim 1 further comprising providing a data recorder communicatively connected to the upper screen or the lower screen.

9. An adjustable wellscreen comprising:
   a base pipe defining a path for fluid communication to a production tubing;
   at least one valve;
   an upper screen located above the valve surrounding at least a portion of the length of the base pipe;
   a valve screen surrounding at least a portion of the valve;
   a lower screen located below the valve surrounding at least a portion of the length of the base pipe;
   a volume defined between the valve screen and the base pipe into which fluids that have flowed through any screen may flow;
   at least one valve motor effective to change the position of the valve;
   at least one sensor effective to determine a physical condition of fluids near the valve and to provide a signal indicative of that physical condition; and
   a controller effective to command the valve motor to change the position of the valve in response to the signal from the sensor;
   wherein the valve is effective to provide controllable communication between the volume and the interior of the base pipe.

10. The wellscreen of claim 9 wherein the sensor detects pressure differential across upper screen or the lower screen.

11. The wellscreen of claim 9 wherein the sensor detects the presence of water.

12. The wellscreen of claim 9 wherein the sensor detects the temperature of fluids flowing through the wellscreen.

13. The wellscreen of claim 9 wherein the sensor detects the phase of fluids passing through the wellscreen.

14. The wellscreen of claim 9 wherein the upper screen and the lower screen have essentially the same lengths.

15. The wellscreen of claim 9 wherein the pressure drop for fluids flowing through the upper screen and the lower screen will be greater than the pressure drop of the fluids flowing from the upper screen and the lower screen to the valve through the volume.

16. The wellscreen of claim 9 wherein the sensor communicates with the controller using wireless communication.

17. The wellscreen of claim 9 wherein the controller communicates with the valve using wireless communications.

18. The wellscreen of claim 9 wherein the valve is powered by an electrical power supply and the sensor communicates with the valve using a time varying electrical signal imposed upon an electrical power supply to the valve.

19. An adjustable well screen assembly comprising:
   a base pipe having an upper end and a lower end;
   an upper screen attached concentrically around the upper end of the base pipe;
   a lower screen attached concentrically around the lower end of the base pipe;
   a valve located between the upper screen and the lower screen; and
   a valve screen attached concentrically around the valve;

wherein the diameter the valve screen is greater than the diameter of the upper screen and the lower screen.

20. The adjustable well screen assembly of claim 19 further comprising:
   a valve motor mechanically connected to said valve, wherein said valve motor opens and closes said valve; and
   a valve controller communicatively connected to said valve motor, wherein said valve controller instructs the valve motor as to a configuration of the valve.

21. The well screen assembly of claim 20 wherein the controller is connected to the valve via a communication means utilizing an electrical cable.

22. The well screen assembly of claim 20 wherein the controller is connected to the valve via a communication means utilizing an optical fiber.

23. The well screen assembly of claim 20 wherein the controller is connected to the valve via a communication means utilizing a hydraulic cable.

24. The well screen assembly of claim 20 wherein the controller is connected to the valve via a communication means utilizing a pneumatic cable.

25. The well screen assembly of claim 20 further comprising a data sensor communicatively connected to the well screen.

26. The well screen assembly of claim 20 further comprising a data transmitter communicatively connected to the well screen.

27. The well screen assembly of claim 20 further comprising at least one data recorder communicatively connected to the well screen.

* * * * *